(12) United States Patent
Choi

(10) Patent No.: US 9,808,220 B2
(45) Date of Patent: Nov. 7, 2017

(54) PROBE FOR ULTRASONIC DIAGNOSTIC APPARATUS

(71) Applicant: SAMSUNG ELECTRONICS CO., LTD., Suwon-si (KR)

(72) Inventor: Jin Young Choi, Chuncheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1206 days.

(21) Appl. No.: 13/712,132

(22) Filed: Dec. 12, 2012

(65) Prior Publication Data

US 2013/0150725 A1 Jun. 13, 2013

(30) Foreign Application Priority Data

Dec. 13, 2011 (KR) .......................... 10-2011-0133504

(51) Int. Cl.
 *A61B 8/00* (2006.01)
 *A61B 8/14* (2006.01)
 *A61B 8/08* (2006.01)

(52) U.S. Cl.
 CPC .............. *A61B 8/4455* (2013.01); *A61B 8/08* (2013.01); *A61B 8/14* (2013.01); *A61B 8/4272* (2013.01);
 (Continued)

(58) Field of Classification Search
 CPC ........ A61B 8/4444; A61B 8/14; A61B 8/4281
 See application file for complete search history.

(56) References Cited

U.S. PATENT DOCUMENTS

| | | | | |
|---|---|---|---|---|
| 5,680,863 | A * | 10/1997 | Hossack | ................... A61B 8/12 600/437 |
| 2002/0022854 | A1 * | 2/2002 | Irion | ................ A61B 17/32002 606/171 |

(Continued)

FOREIGN PATENT DOCUMENTS

| | | |
|---|---|---|
| CN | 1117275 A | 2/1996 |
| CN | 101589958 A | 12/2009 |

(Continued)

OTHER PUBLICATIONS

Communication dated Apr. 29, 2013 issued by the Korean Intellectual Property Office in counterpart Korean Patent Application No. 10-2011-0133504.

(Continued)

*Primary Examiner* — Joseph M Santos Rodriguez
(74) *Attorney, Agent, or Firm* — Sughrue Mion, PLLC

(57) ABSTRACT

A probe for an ultrasonic diagnostic apparatus which is used for performing a test upon a subject is provided. The probe includes a case which forms an exterior of the probe, a piezoelectric object which is provided on an inside of the case and which generates an ultrasonic wave, a sound absorbing layer which is provided at a rear surface of the piezoelectric object and which prevents the ultrasonic wave from being delivered to a rear portion of the piezoelectric object, an acoustic matching layer which delivers the generated ultrasonic wave to a subject by matching a sound impedance of the piezoelectric object with a sound impedance of the subject, and a sound lens which concentrates the generated ultrasonic wave and radiates the concentrated ultrasonic wave toward the subject.

18 Claims, 6 Drawing Sheets

(52) U.S. Cl.
CPC .......... *A61B 8/4281* (2013.01); *A61B 8/4444* (2013.01); *A61B 8/4494* (2013.01); *A61B 8/4461* (2013.01)

(56) References Cited

U.S. PATENT DOCUMENTS

| | | |
|---|---|---|
| 2005/0124889 A1 | 6/2005 | Flesch |
| 2008/0312537 A1* | 12/2008 | Hyuga ................. B06B 1/0622 600/459 |
| 2009/0299194 A1* | 12/2009 | Matsuzawa .............. A61B 8/14 600/459 |
| 2011/0087107 A1 | 4/2011 | Lindekugel et al. |
| 2011/0319768 A1* | 12/2011 | Saito ..................... G10K 11/30 600/472 |

FOREIGN PATENT DOCUMENTS

| | | | | |
|---|---|---|---|---|
| FR | 2580079 A1 * | 10/1986 | ......... | G01S 7/52046 |
| KR | 10-1086048 A | 11/2011 | | |
| WO | WO 2010029556 A1 * | 3/2010 | ............... | A61B 8/08 |
| WO | WO 2010100921 A1 * | 9/2010 | ........... | A61B 8/4281 |

OTHER PUBLICATIONS

Communication dated Jun. 15, 2015, issued by the State Intellectual Property of P.R. China, in counterpart Chinese Application No. 201210539225.5.

* cited by examiner

PROBE FOR ULTRASONIC DIAGNOSTIC APPARATUS

CROSS-REFERENCE TO RELATED APPLICATION

This application claims priority from Korean Patent Application No. 10-2011-0133504, filed on Dec. 13, 2011 in the Korean Intellectual Property Office, the disclosure of which is incorporated herein by reference in its entirety.

BACKGROUND

1. Field

Exemplary embodiments relate to a probe for use in conjunction with an ultrasonic diagnostic apparatus, and more particularly, to a probe for use in conjunction with an ultrasonic diagnostic apparatus which is capable of performing a test by closely adhering to a particular portion of a test subject.

2. Description of the Related Art

In general, an ultrasonic diagnostic apparatus is an apparatus which is configured to radiate an ultrasonic signal toward a desired portion at an inside of a body from the surface of a subject and to obtain an image with reference to a cross section of a soft tissue or a blood flow by using the information included in the reflected ultrasonic signal in an non-invasive manner. The apparatus as such, as compared with other display apparatuses such as an X-ray photographing apparatus, a CT apparatus (Computerized Tomography Scanner), an MRI (Magnetic Resonance Image), or a nuclear medical diagnostic device, is smaller in size, less expensive, and capable of displaying images obtained in real time, and is not exposed to radiation of an X-ray, and thus relatively safer, thereby being used widely for the diagnosis of medical conditions relating to hearts, abdomens, genital organs, and in gynecology.

In particular, an ultrasonic diagnostic apparatus includes a probe which is configured to transmit an ultrasonic signal to a subject in order to obtain an ultrasonic image of the subject and to receive an echo signal that is reflected from the subject.

A probe includes a transducer, a case which is provided with an open upper end thereof, and a cover portion which is coupled to the open upper end of the case in order to directly contact with a surface of the subject.

A transducer includes a piezoelectric layer which is configured to reciprocally change an electrical signal and a sound signal as a piezoelectric object vibrates, an acoustic matching layer which is configured to reduce a difference of a sound impedance between the piezoelectric layer and the subject so that the ultrasonic wave generated at the piezoelectric layer is delivered primarily to the subject, a lens layer which is configured to concentrate the ultrasonic wave which proceeds to a front portion of the piezoelectric layer to a certain position, and a sound absorbing layer which is configured to reduce a distortion of an image by preventing the ultrasonic wave from proceeding to a rear portion of the piezoelectric layer.

A probe which is configured for use in conjunction with an ultrasonic diagnostic apparatus includes at least one of a concave-type probe which is used for a diagnosis relating to an abdomen and which has a concave surface thereof, a linear-type probe which is used for a diagnosis relating to one or more of breasts, a thyroid, and testicles and which has a flat surface thereof, an endocavity-type probe which is used for a diagnosis relating to a uterus and an ovary, and a hockey stick-type probe.

A muscular skeletal system (for example, shoulders and knees) having a curved surface thereof may not be convenient for using a linear-type probe provided with a flat surface thereof, as a footprint of the probe has a length which falls approximately within a range of between 40 mm and 50 mm, and thus the probe may not closely adhere to the curved surface of the subject. Therefore, multiple uses of a probe having a small footprint, such as a hockey stick probe, are required in order to perform a scan, and in a case in which a probe other than a linear-type probe is used, the probe may not be closely in contact with the subject, as the body figure of the subject and the shape of a probe may not be in correspondence to each other.

In addition, when an ultrasonic test is performed, an ultrasonic wave does not penetrate a bone and air, so in a case in which a probe configured for an ultrasonic diagnostic apparatus directly contacts the skin of the subject, the collection of data is not possible. Thus, in a case in which an ultrasonic wave diagnosis is being performed, a liquid is typically applied on the skin in order to eject the air which is situated in between the probe and the skin of the subject, or a pad provided with a liquid applied thereon is used.

SUMMARY

Therefore, it is an aspect of exemplary embodiments described herein to provide a probe which is configured for use in conjunction with an ultrasonic diagnostic apparatus that may be used for a diagnosis of a medical condition relating to a muscular skeletal system of a subject.

Additional aspects of the exemplary embodiments will be set forth in part in the description which follows and, in part, will be obvious from the description, or may be learned by practice of the exemplary embodiments.

In accordance with one aspect of one or more exemplary embodiments, a probe for use in conjunction with an ultrasonic diagnostic apparatus includes a case, a piezoelectric object, a sound absorbing layer, an acoustic matching layer and a sound lens. The case may form an exterior of the probe. The piezoelectric body may be provided at an inside of the case and may generate an ultrasonic wave. The sound absorbing layer may be provided at a rear surface of the piezoelectric object and may prevent the ultrasonic wave from being delivered to a rear portion of the piezoelectric object. The acoustic matching layer may be provided at a front surface of the piezoelectric object and may deliver the generated ultrasonic wave to a subject by matching a sound impedance of the piezoelectric object with a sound impedance of the subject. The sound lens may be provided at a front surface of the acoustic matching layer and may concentrate the generated ultrasonic wave and radiate the concentrated ultrasonic wave toward the subject. The sound lens may include a concave portion which facilitates performance of a diagnosis along a curved surface of the subject.

The probe may further include a moving layer which is provided at a rear surface of the sound absorbing layer and which changes a radius of curvature of the sound lens, and a driving member which causes the moving layer to move.

The moving layer may include compressed gas.

The moving layer may include a liquid and a film surrounding the liquid.

The probe may further include a cover portion which is provided at a front surface of the sound lens and which makes contact with a skin of the subject. The cover portion may include a concave portion having a same shape as a shape of the concave portion of the sound lens.

The probe may further include a pad which is protrudingly provided at a front surface of the cover portion and which ejects air from a contact surface at which the probe makes contact with the skin of the subject.

The pad may be integrally attached to the sound lens.

The pad may be provided at an outer side of a base member that is detachably mounted to the cover portion.

The driving member may be positioned at a rear surface of the moving layer, and may include a piston which causes the moving layer to move.

Each of a radius of curvature of the piezoelectric object and a radius of curvature of the sound absorbing layer may vary as the moving layer is moved by using the piston, and the concave portion may flatten as the moving layer is moved.

The driving member may further include a motor which is coupled to the piston and which drives the piston in a full automatic manner.

Each of a radius of curvature of the piezoelectric object and a radius of curvature of the sound absorbing layer may vary when the piston is driven in a full automatic manner such that the moving layer is moved, and the concave portion may flatten as the moving layer is moved.

The cover portion may include a flexible material.

In accordance with another aspect of one or more exemplary embodiments, a probe for use in conjunction with an ultrasonic diagnostic apparatus is provided. The probe includes a cover portion which forms an exterior of the probe and a transducer which is provided at an inner side of the cover portion and which reciprocally changes an electrical signal and a sound signal. A first surface of the transducer may include a concave portion which facilitates performance of a diagnosis along a curved surface of a subject, and a second surface of the transducer may include a moving layer which changes a radius of curvature of a portion of the transducer which makes contact with the subject.

The probe may include a pad which is attached to a front surface of the cover portion and which ejects air from a contact surface at which the probe makes contact with a skin of the subject.

The probe may further include a base portion which is detachably provided at the cover portion.

A pad may be provided at an outer side of the base portion. The pad may eject air from a contact surface at which the probe makes contact with a skin of the subject.

The cover portion may include a concave portion having a same shape as a shape of the concave portion of the first surface of the transducer.

The probe may further include a driving member which is positioned at a rear surface of the moving layer and which causes the moving layer to move.

The driving member may include a piston which causes the moving layer to move, and a motor which is coupled to the piston and which drives the piston in a full automatic manner.

As described above, exemplary embodiments capable of facilitating performance of a diagnosis of a medical condition relating to a subject at a single scan in a case in which a medical condition relating to a muscular skeletal system (for example, shoulders and knees) is being diagnosed.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
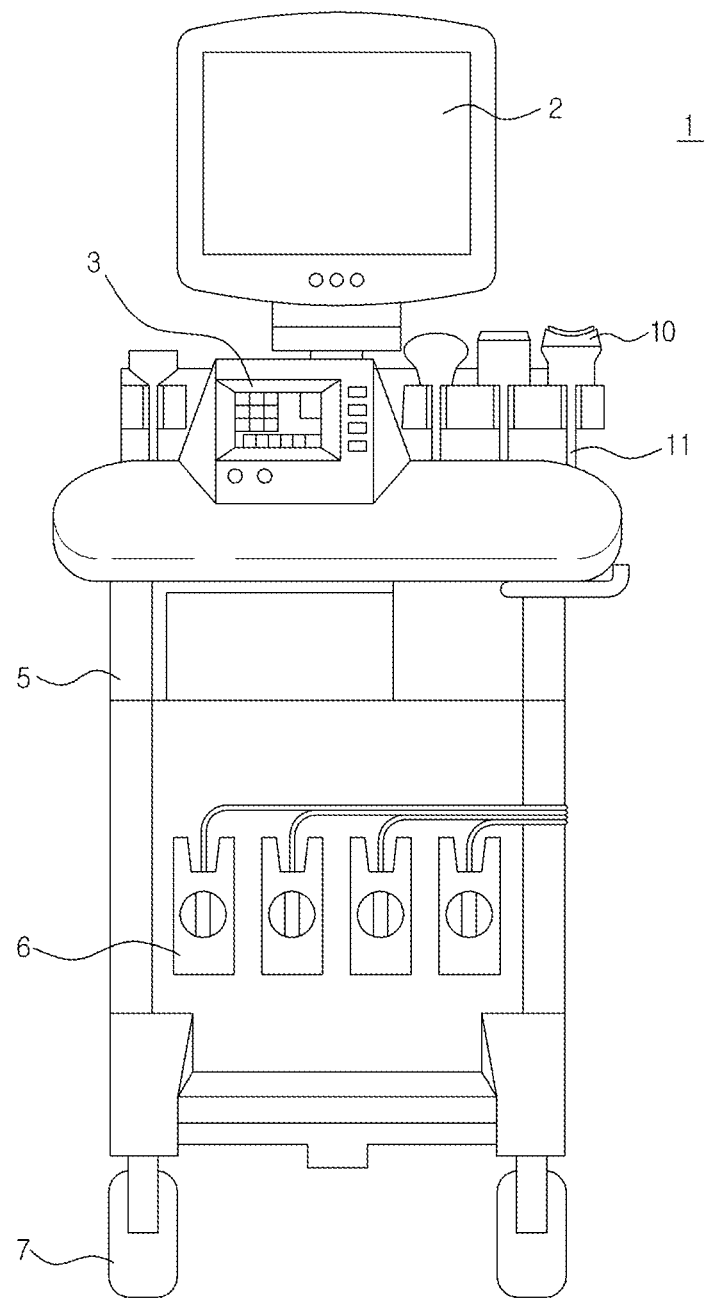
FIG. 1 is a drawing which illustrates a front surface of an ultrasonic diagnostic apparatus, in accordance with an exemplary embodiment.

Reference will now be made in detail to exemplary embodiments, examples of which are illustrated in the accompanying drawings, wherein like reference numerals refer to like elements throughout.

FIG. 1 is a drawing which illustrates a front surface of an ultrasonic diagnostic apparatus, according to an exemplary embodiment. A probe according to one or more exemplary embodiments is not only used in conjunction with an ultrasonic diagnostic apparatus, but also is used in conjunction with various ultrasonic transducer apparatuses, and a probe for use in conjunction with an ultrasonic diagnostic apparatus will be described hereinafter as an example.

As illustrated in FIG. 1, an ultrasonic diagnostic apparatus 1 according to an exemplary embodiment is provided with a probe 10 having various types thereof for use in conjunction with the ultrasonic diagnostic apparatus. The probe 10 radiates an ultrasonic wave toward a subject and receives an echo of the ultrasonic wave from the subject. The ultrasonic diagnostic apparatus 1 is further provided with a control button 3, and a display apparatus 2 installed thereto, and includes a body 5 which is used for generating an image of the subject. The probe 10 for use in conjunction with the ultrasonic diagnostic apparatus 1 is connected to the body 5 by a cable 11 and a connector 6 that are integrally connected to the probe 10. At a lower side of the body 5, a supporting portion 7 which supports the ultrasonic diagnostic apparatus 1 is provided. The supporting portion 7 may include a transporting medium, such as, for example, wheels, which transporting medium is used for moving the ultrasonic diagnostic apparatus 1.

Figure 2:
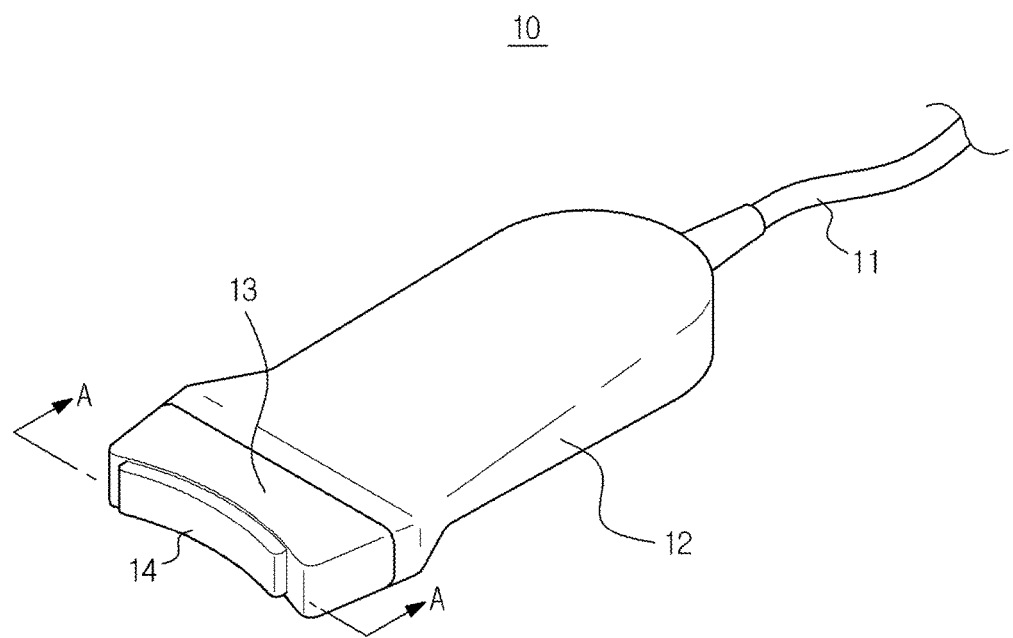
FIG. 2 is a perspective view which illustrates a probe which is configured for use in conjunction with an ultrasonic diagnostic apparatus, in accordance with an exemplary embodiment.
Figure 3:
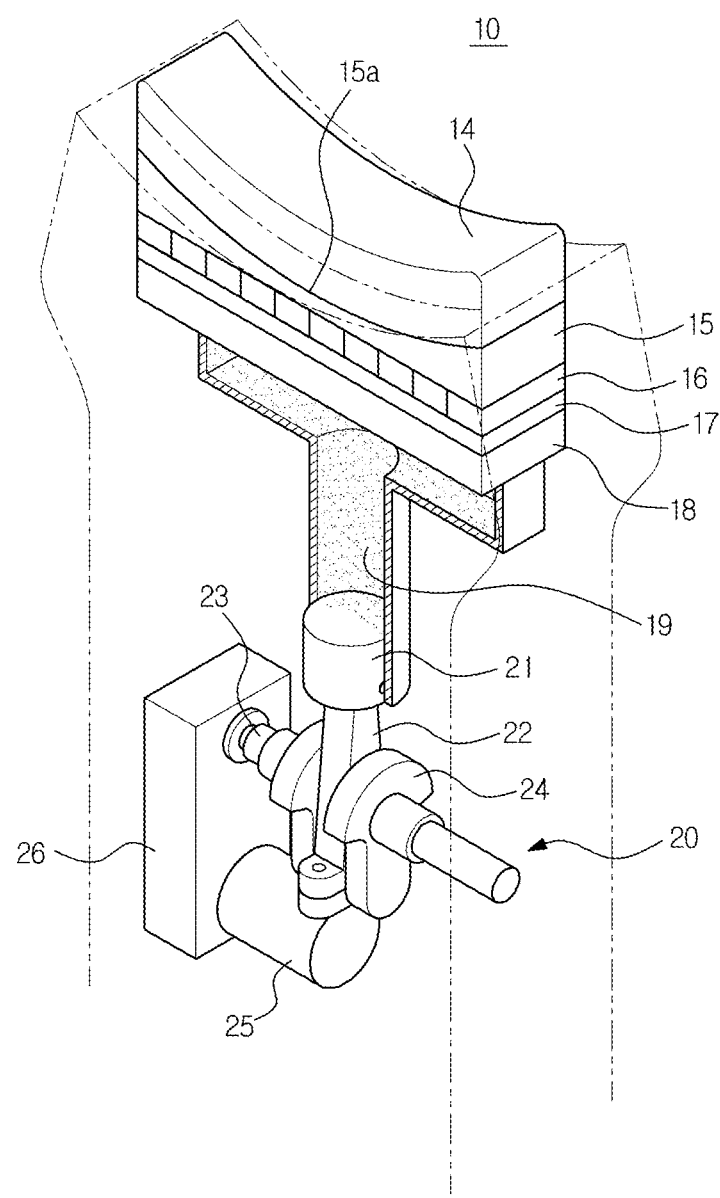
FIG. 3 is a perspective view which illustrates a cross section A-A as indicated in FIG. 2.
Figure 4:
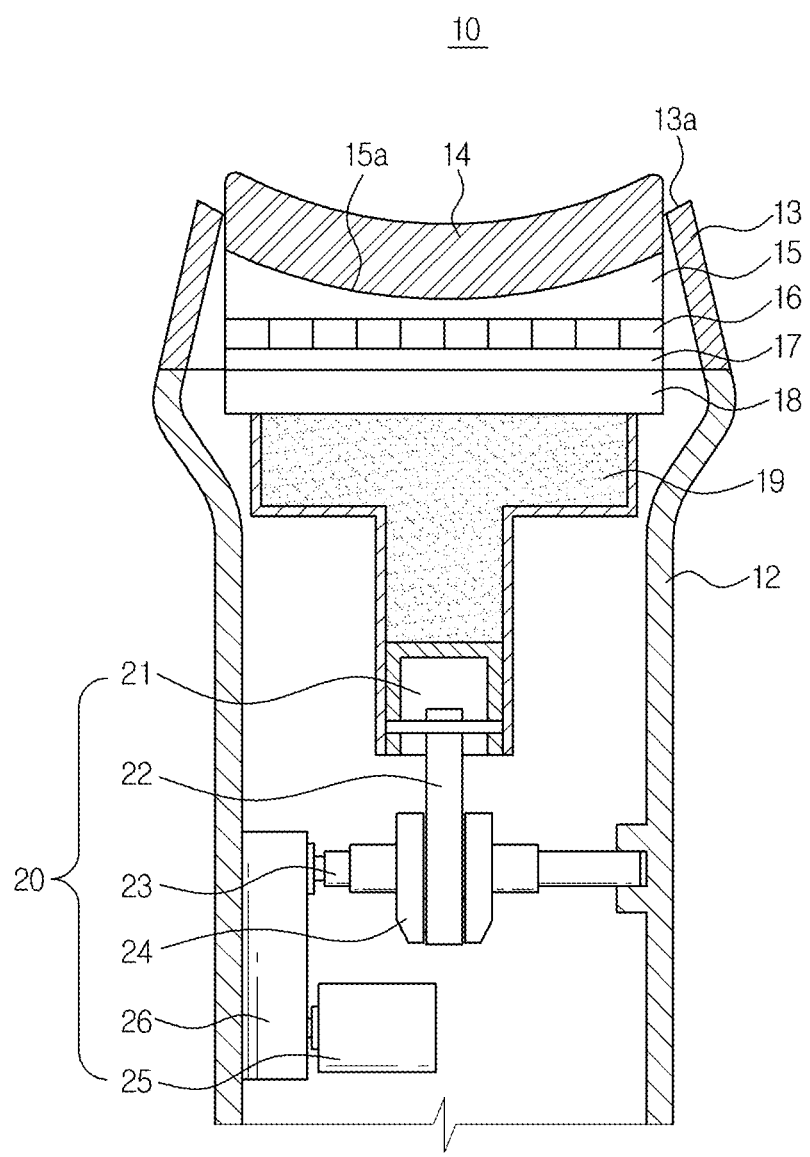
FIG. 4 is a cross-sectional view which illustrates a cross section A-A as indicated in FIG. 2.

FIG. 2 is a perspective view which illustrates a probe which is configured for use in conjunction with an ultrasonic diagnostic apparatus, according to an exemplary embodiment, FIG. 3 is a perspective view which illustrates a cross section A-A as indicated in FIG. 2, and FIG. 4 is a cross-sectional view which illustrates a cross section A-A as indicated in FIG. 2.

As illustrated in FIGS. 2, 3, and 4, the probe 10 for use in conjunction with the ultrasonic diagnostic apparatus 1 includes a case 12 which forms an exterior of the probe 10 and a cover portion 13 which is provided at an upper side of the probe 10. An upper side of the case 12 is open, and the cover portion 13 is coupled to an upper end of the case 12 which is open. An administrator may perform a test by holding the case 12 of the probe 10 and causing the cover portion 13 to make contact with the subject.

At an inner side of the cover portion 13, a transducer is provided. The transducer includes a piezoelectric object 17, an acoustic matching layer 16, a sound lens 15, and a sound absorbing layer 18.

The sound lens 15, the acoustic matching layer 16, the piezoelectric object 17, and the sound absorbing layer 18 are arranged in an order of appearance as the above from a front surface portion at which the contact is made with the subject.

The piezoelectric object 17 is positioned at an inner side of the cover portion 13, and is attached at a front surface of the sound absorbing layer 18. Electrode portions (not shown) are provided at both sides of the piezoelectric object 17. The piezoelectric object 17 converts an electrical signal to an ultrasonic wave, which is a sound signal, in order to release the ultrasonic wave into air, and converts the ultrasonic wave, which is reflected from the air, to an electrical signal, in order to transmit the electric signal to an apparatus.

The piezoelectric object 17 is configured to generate an ultrasonic wave by using a resonance phenomenon, and may be formed by using at least one of a ceramic from a lead zirconate ceramic material, such as, for example, lead zirconate titanate (PZT), a PNZT single crystal which is made of the solid solution of zinc niobate and titanate, and a PMZT single crystal which is made of the solid solution of magnesium niobate and titanate.

In a case of the electrode portions (not shown) formed at both sides of the piezoelectric object 17, the electrode portions may be formed by using a metal which has a relatively high conductivity, such as, for example, at least one of gold, silver, and copper, or by using graphite.

The acoustic matching layer 16 is installed at a front portion of the piezoelectric object 17. The acoustic matching layer 16 matches the sound impedance of the piezoelectric object 17 with the sound impedance of the subject, so that the ultrasonic wave signal generated by the piezoelectric object 17 may be efficiently delivered to the subject. Accordingly, the acoustic matching layer 16 is configured to have a median sound impedance value with respect to the sound impedance of the piezoelectric object 17 and the sound impedance of the subject.

The acoustic matching layer 16 may be formed by using a glass material or a resin material. The acoustic matching layer 16 may include a plurality of acoustic matching layers which have different respective materials so that the sound impedance may be gradually changed from the sound impedance of the piezoelectric object 17 to the sound impedance of the subject.

The sound absorbing layer 18 is disposed at a rear portion of the piezoelectric object 17. The sound absorbing layer 18 restrains a free vibration of the piezoelectric object 17 in order to reduce the width of the pulse of the ultrasonic wave, and blocks the ultrasonic wave which would otherwise be transmitted to a rear portion of the piezoelectric object 17, thereby preventing a distortion of an resultant image.

A printed circuit board (PCB) (not shown) may be positioned in between the sound absorbing layer 18 and the piezoelectric object 17. The PCB is provided in order to reciprocally change the electrical signal and the ultrasonic wave signal generated by the electrode portion (not shown). The PCB may be arranged vertically with respect to a side surface of the piezoelectric object 17 having a largest surface area, and the sound absorbing layer 18 may be arranged such that the PCB and the sound absorbing layer 18 are stacked up against each other. The PCB may further include a structure, such as, for example, a flexible printed circuit board (FPCB) which is provided in conjunction with a signal, which structure is capable of supplying electrical energy.

The sound lens 15 is disposed at a front portion of the acoustic matching layer 16. The sound lens 15 is configured to concentrate the ultrasonic wave signal, which proceeds to a front of the sound lens 15, to a particular position. The sound lens 15 includes a concave portion 15a which facilitates performance of a diagnosis along a curved surface of the subject.

The cover portion 13 may also be provided with a concave portion 13a which has a same shape as a shape of the concave portion 15a of the sound lens 15. However, in a case in which the cover portion 13 is formed by using a flexible material, the cover portion 13 does not need to be provided with the concave portion 13a, because the flexibility of the material ensures that the probe 10 remains fully capable of facilitating performance of a diagnosis on the surface of the subject.

In addition, at a rear surface of the sound absorbing layer 18, a moving layer 19 which changes the radius of curvature of the sound lens 15 with respect to making contact with the subject is provided. At a rear of the moving layer 19, a driving member 20 is provided, which driving member 20 causes the moving layer 19 to move in order to change the radius of curvature of the sound lens 15.

The moving layer 19 may be provided, for example, as pressured gas. The moving layer 19 may be formed by using a liquid, and in this case as such, the moving layer 19 includes a film which surrounds the liquid. The film which is included within the moving layer 19 may be formed by using a thin film so that the shape of the moving layer 19 may be changed. In addition, the liquid which is surrounded by the film may be formed by using an oil film having viscosity and flexibility.

The driving member 20, which is positioned at a rear portion of the moving layer 19, may include a piston 21 which causes the moving layer 19 to move. The piston 21 is connected to a control member, such as a lever (not shown) which is provided at an outer side of the case 12, so that an administrator may manually control the position of the piston 21, and accordingly, the moving layer 19 may be moved. Each of a radius of a curvature of the piezoelectric object 17 and a radius of a curvature of the sound absorbing layer 18 varies as the moving layer 19 is moved by the piston 21, and accordingly, a radius of a curvature of the sound lens 15 also varies. Thus, the shape of the concave portion 15A may flatten, such that a concave-type probe may be deformed to be shaped similarly as a linear-type probe.

In addition, the piston 21 may be operated in a full automatic manner by being connected to a motor 25. In this case, an administrator operates the motor 25 by using a control member, such as a button (not shown) positioned at an outer side of the case 12, and accordingly, the piston 21 may be operated. A structure, such as a crank shaft 23, a crank arm 24, and/or a connecting rod 22, may be further provided for translating a rotational movement of the motor 25 to a reciprocal movement of the piston 21. In addition, a reduction gear 26 may be provided for controlling a speed of the rotation of the motor 25.

According to an exemplary embodiment, the motor 25 is connected to the reduction gear 26, and the reduction gear 26 is connected to the connecting rod 22 through the crank shaft 23. The rotational movement of the crank shaft 23 is translated to the reciprocal movement of the piston 21 through the connecting rod 22. A crank journal may be coupled to the crank shaft 23 in order to fix the crank shaft 23. One side of the connecting rod 22 is connected to the crank shaft 23 while the other side of the connecting rod 22 is coupled to the piston 21. Accordingly, the driving force of the motor 25 is delivered to the piston 21, and as the piston 21 moves, the moving layer 19 may also be moved, and based on the movement of the moving layer 19, the radius of curvature of the transducer having the sound lens 15 varies. The variations of the radius of curvature of the piezoelectric material 17 and radius of curvature of the sound absorbing layer 18 follow the movement of the moving layer 19, and the variation of the radius of curvature of the sound lens 15 remains the same, regardless of whether the piston 21 operates manually or automatically. Accordingly, in a case in which a body structure of the subject is different than the body structure of a previous subject, the radius of curvature of the sound lens 15 may be changed to a certain degree, and thus a performance of a diagnosis by using the same probe 10 in conjunction with the ultrasonic diagnostic apparatus 1 may be possible.

In addition, at a rear surface of the driving member 20, a strain relief apparatus (not shown) which connects the cable 11 to the probe 10 is provided. The strain relief apparatus is configured to protect the cable 11 from an impact applied to the cable 11, and is capable of restraining the impact, which is caused by a curvature of the cable 11, which would otherwise be applied to an outer side of the probe 10 and to a contact point of the cable 11.

According to an exemplary embodiment, a pad 14 is integrally attached to the cover portion 13. Because an ultrasonic wave does not penetrate through a bone and air, in a case in which an ultrasonic diagnosis is being performed, an ultrasonic wave mediating material is applied in between the body of the subject and the probe 10. In particular, a middle layer which is included within the ultrasonic wave mediating material is needed so that the ultrasonic wave radiated toward an inside of a human body is evenly spread and then the wave signal is reflected back toward the body 5.

In a case in which the conventional ultrasonic wave mediating material is of a liquid type, most of the substance thereof is formed with moisture, and thereby becomes evaporated or displaced to a separate portion of the skin of a subject after a certain period of time elapses after the mediating material has been applied on the skin of the subject and the probe 10 has been operated thereon, and thus a continuous usage thereof is not possible. In addition, the conventional ultrasonic wave mediating material of a liquid type is less useful for obtaining an image of an organ which is located on a curved portion or at a position which is relatively proximate to a curved portion of the body of the subject.

Thus, in an exemplary embodiment, a pad which has the ultrasonic wave mediating material applied thereto by using a cross-linked polymer is used instead. However, in a case of the pad, an administrator must carry the pad separately, and in a case of performing a diagnosis, the pad must be held with one hand while the other hand is used for operating the probe 10.

In order to remove the above constraints, the probe 10 according to an exemplary embodiment is provided with the pad 14, which has the ultrasonic wave mediating material applied thereto by using a cross-linked polymer, mounted thereto for use. According to an exemplary embodiment, the pad 14 is integrally attached to the sound lens 15, and the pad 14 protrudes through an opening portion of the cover portion 13. In addition, the pad 14 may be attached to a front surface of the cover portion 13. Thus, the pad 14 may be placed into direct contact with the skin of the subject, and accordingly, a test may be performed without using a separate ultrasonic wave mediating material. The foregoing aspect as such may provide an advantage in view of a recent trend in which an administrator performs a diagnosis relating to the subject while simultaneously performing other activities. Further, the foregoing aspect may also provide an advantage relating to an improvement in a compactness of the diagnostic apparatus.

Figure 5:
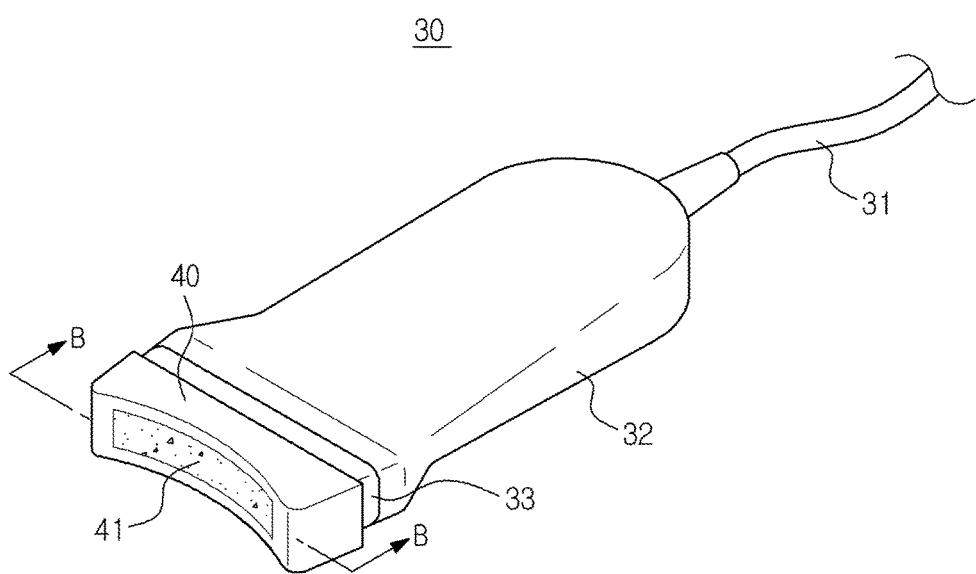
FIG. 5 is a perspective view which illustrates a probe which is configured for use in conjunction with an ultrasonic diagnostic apparatus, in accordance with another exemplary embodiment.
Figure 6:
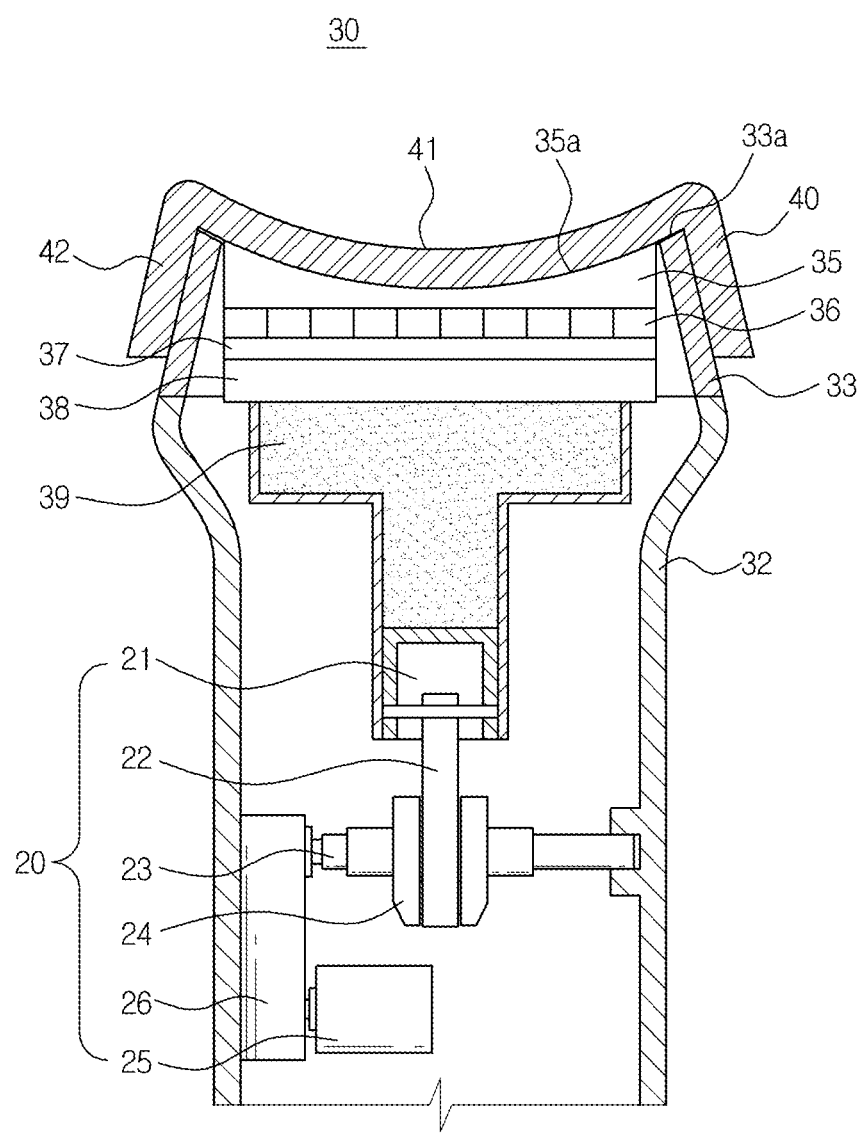
FIG. 6 is a cross-sectional view which illustrates a cross section B-B as indicated in FIG. 5.

FIG. 5 is a perspective view which illustrates a probe configured for use in conjunction with an ultrasonic diagnostic apparatus, according to another exemplary embodiment, and FIG. 6 is a cross-sectional view which illustrates a cross section B-B as indicated in FIG. 5.

As illustrated in FIGS. 5 and 6, a probe 30 for use in conjunction with an ultrasonic diagnostic apparatus according to another exemplary embodiment further includes a base member 40 which is detachably mounted to a cover portion 33. The probe 30 also includes a cable 31, which is similar to the cable 11 described above with respect to FIG. 2; a concave portion 33a of the cover portion 33, which is similar to the concave portion 13a of the cover portion 13 described above with respect to FIG. 4; an acoustic matching layer 36 which is similar to the acoustic matching layer 16 described above with respect to FIGS. 3 and 4; and a piezoelectric object 37 which is similar to the piezoelectric object 17 described above with respect to FIGS. 3 and 4. A further detailed description of these items will therefore be omitted for brevity.

As illustrated in FIGS. 5 and 6, a sound lens 35 of the probe 30 may further include a concave portion 35a. In addition, a moving layer 39 which changes the radius of curvature of the sound lens 35 may be provided at a rear surface of an sound absorbing layer 38, and a driving member 20 may be provided at a rear surface of the moving layer 39 for causing the moving layer 39 to move. The base member 40 may include a concave portion 41 which has a shape which is similar to a shape of the concave portion 35a of the sound lens 35, and the concave portion 41 of the base member 40 facilitates performance of a diagnosis by increasing a contact area with respect to the skin of the subject.

The base member 40 may be provided with a guide portion 42 so that the base member 40 may be inserted into the probe 30. The guide portion 42 extends from the concave portion 41 of the base member 40, and may be provided in a shape which corresponds to a case 32 and the cover portion 33 such that the guide portion 42 may be inserted into the case 32 and the cover portion 33 of the probe 30. In addition, the base member 40 may be formed by using an elastic material, and the elasticity of the material may enable the base member 40 to be inserted into the probe 30, although a size of the probe 30 may vary.

The concave portion 41 of the base member 40 may be provided with a pad (not shown), and the pad makes contact with the skin of the subject. Because the pad must adhere as closely as possible to the skin of the subject in order to minimize a loss of energy from the ultrasonic wave, the concave portion 41 of the case member 40, which is positioned in between the pad and the sound lens 35, may be provided such that a thickness of the concave portion 41 is as thin as possible.

The pad is provided at the base member 40, and the base member 40 is inserted into the probe 30 at the time of performing a diagnosis. In a case in which the base member 40 is provided with the pad, the base member 40 may be detached to be stored separately when the probe 30 is not being used.

Although a few exemplary embodiments have been shown and described, it will be appreciated by those skilled in the art that changes may be made in these exemplary embodiments without departing from the principles and spirit of the present disclosure, the scope of which is defined in the claims and their equivalents.

What is claimed is:

1. A probe for an ultrasonic diagnostic apparatus, comprising:
   a case which forms an exterior of the probe;
   a piezoelectric object which is provided at an inside of the case and which generates an ultrasonic wave;
   a backing layer which is provided at a rear surface of the piezoelectric object and which prevents the generated ultrasonic wave from being delivered to a rear portion of the piezoelectric object;
   an acoustic matching layer which is provided at a front surface of the piezoelectric object and which delivers the generated ultrasonic wave from the piezoelectric object to a subject by matching a sound impedance of the piezoelectric object with a sound impedance of the subject;
   a single acoustic lens which is provided at a front surface of the acoustic matching layer and which concentrates the generated ultrasonic wave and radiates the concentrated ultrasonic wave toward the subject;
   a moving layer which is provided at a rear surface of the backing layer and which changes a radius of curvature of the acoustic lens, and
   a driving member which causes the moving layer to move,
   wherein the moving layer comprises a liquid and a film surrounding the liquid, and
   wherein the single acoustic lens includes a concave portion which facilitates performance of a diagnosis along a curved surface of the subject, and has a varying radius of curvature.

2. The probe for an ultrasonic diagnostic apparatus of claim 1, further comprising:
   a cover portion which is provided at a front surface of the acoustic lens and which is configured to make contact with a skin of the subject, wherein the cover portion includes a concave portion having a same shape as a shape of the concave portion of the acoustic lens.

3. The probe for an ultrasonic diagnostic apparatus of claim 2, further comprising:
   a pad which is protrudingly provided at a front surface of the cover portion and which ejects air from a contact surface at which the probe is configured to make contact with the skin of the subject.

4. The probe for an ultrasonic diagnostic apparatus of claim 3, wherein the pad is integrally attached to the acoustic lens.

5. The probe for an ultrasonic diagnostic apparatus of claim 3, wherein the pad is provided at an outer side of a base member that is detachably mounted to the cover portion.

6. The probe for an ultrasonic diagnostic apparatus of claim 1, wherein the driving member includes a piston located on a rear surface of the moving layer and configured to move the moving layer.

7. The probe for an ultrasonic diagnostic apparatus of claim 6, wherein each of a radius of curvature of the piezoelectric object and a radius of curvature of the backing layer varies as the moving layer is moved by using the piston, and the concave portion flattens as the moving layer is moved.

8. The probe for an ultrasonic diagnostic apparatus of claim 6, wherein the driving member further includes a motor which is coupled to the piston and which drives the piston in a full automatic manner.

9. The probe for an ultrasonic diagnostic apparatus of claim 8, wherein each of a radius of curvature of the piezoelectric object and a radius of curvature of the backing layer varies when the piston is driven in a full automatic manner such that the moving layer is moved, and the concave portion flattens as the moving layer is moved.

10. The probe for an ultrasonic diagnostic apparatus of claim 2, wherein the cover portion includes a flexible material.

11. An ultrasonic diagnostic apparatus comprising a probe including a cover portion in contact with a subject and a transducer which is disposed on a rear surface of the cover portion and having a piezoelectric object, an acoustic matching layer, a single acoustic lens, and a backing layer which are configured to inter-convert an electrical signal and a sound signal,
    wherein the probe comprises:
      a concave portion disposed to be inwardly recessed on a surface of the transducer in contact with the cover portion and configured to diagnose the subject along a curved surface of the subject; and
      a moving layer disposed on a rear surface of the transducer and configured to change a radius of curvature of a portion of the single acoustic lens which is configured to make contact with the subject,
    wherein the moving layer comprises a liquid and a film surrounding the liquid.

12. The ultrasonic diagnostic apparatus of claim 11, further comprising:
    a pad which is attached to a front surface of the cover portion and which ejects air from a contact surface at which the probe is configured to make contact with a skin of the subject.

13. The ultrasonic diagnostic apparatus of claim 11, further comprising:
    a base portion which is detachably provided at the cover portion.

14. The ultrasonic diagnostic apparatus of claim 13, further comprising a pad which is provided at an outer side of the base portion and which ejects air from a contact surface at which the probe is configured to make contact with a skin of the subject.

15. The ultrasonic diagnostic apparatus of claim 11, wherein the cover portion includes a concave portion having a same shape as a shape of the concave portion of the first surface of the transducer.

16. The ultrasonic diagnostic apparatus of claim 11, further comprising:
    a driving member which is positioned at a rear surface of the moving layer and which causes the moving layer to move.

17. The ultrasonic diagnostic apparatus of claim 16, wherein the driving member includes a piston which causes the moving layer to move, and a motor which is coupled to the piston and which drives the piston in a full automatic manner.

18. A probe for an ultrasonic diagnostic apparatus, comprising:
- a case which forms an exterior of the probe;
- a piezoelectric object which is provided at an inside of the case and which generates an ultrasonic wave;
- a backing layer which is provided at a rear surface of the piezoelectric object and which prevents the generated ultrasonic wave from being delivered to a rear portion of the piezoelectric object;
- an acoustic matching layer which is provided at a front surface of the piezoelectric object and which delivers the generated ultrasonic wave to a subject by matching a sound impedance of the piezoelectric object with a sound impedance of the subject;
- a single acoustic lens which is provided at a front surface of the acoustic matching layer and which concentrates the generated ultrasonic wave and radiates the concentrated ultrasonic wave toward the subject;
- a concave portion disposed on the sound lens and configured to diagnose the subject along a curved surface of the subject; and
- a moving layer disposed on a rear surface of the backing layer and configured to change radius of curvature of the single acoustic lens,
- wherein the moving layer comprises a liquid and a film surrounding the liquid.

* * * * *